United States Patent
McMinn et al.

(10) Patent No.: US 8,764,844 B2
(45) Date of Patent: *Jul. 1, 2014

(54) JOINT PROSTHESIS

(75) Inventors: Derek James Wallace McMinn, Birmingham (GB); Thomas Burton Pynsent, Feckenham (GB)

(73) Assignee: T.J. Smith & Nephew, Limited, Hull (GB)

( * ) Notice: Subject to any disclaimer, the term of this patent is extended or adjusted under 35 U.S.C. 154(b) by 61 days.

This patent is subject to a terminal disclaimer.

(21) Appl. No.: 12/738,305

(22) PCT Filed: Oct. 22, 2008

(86) PCT No.: PCT/GB2008/003579
§ 371 (c)(1),
(2), (4) Date: Jun. 8, 2010

(87) PCT Pub. No.: WO2009/053690
PCT Pub. Date: Apr. 30, 2009

(65) Prior Publication Data
US 2010/0298949 A1   Nov. 25, 2010

(30) Foreign Application Priority Data

Oct. 22, 2007  (GB) .................................. 0720596.6

(51) Int. Cl.
*A61F 2/36* (2006.01)
(52) U.S. Cl.
USPC .................. 623/22.44; 623/23.21; 623/23.26; 623/23.31; 623/23.35
(58) Field of Classification Search
USPC ............ 623/22.11, 22.12, 22.15, 22.4–22.46, 623/23.11–23.15, 23.18–23.29, 23.31, 623/23.35, 23.39, 23.4, 23.44
See application file for complete search history.

(56) References Cited

U.S. PATENT DOCUMENTS

| 2,650,588 A | * | 9/1953 | Drew .......................... 623/23.11 |
| 2,679,245 A | * | 5/1954 | Timmermans ............. 623/23.11 |
| 2,685,877 A | * | 8/1954 | Dobelle ..................... 623/23.11 |
| 2,718,228 A | * | 9/1955 | Van Steenbrugghe ..... 623/23.14 |
| 4,783,192 A | * | 11/1988 | Wroblewski et al. ...... 623/23.21 |
| 4,944,762 A | * | 7/1990 | Link et al. .................. 623/23.21 |
| 5,571,203 A | | 11/1996 | Masini |

(Continued)

FOREIGN PATENT DOCUMENTS

| EP | 0 579 868 A2 | 1/1994 |
| EP | 0 666 069 A1 | 8/1995 |

(Continued)

OTHER PUBLICATIONS

International Search Report, PCT/GB2008/003579, 4 pages.

(Continued)

*Primary Examiner* — Marcia Hoffman
(74) *Attorney, Agent, or Firm* — Krieg DeVault LLP

(57) ABSTRACT

An implant stem (1, 2) for implantation in a femur, comprising: a base portion (3) disposed at the proximal end (4) of the stem and a stem portion (5) extending to the distal end (6) of the stem, wherein the base portion (3) has an engagement means (7) for engaging, in use, with the resected end of the femur. An implant comprising such a stem (1, 2) and a head. A method for implanting such implants in a femur.

18 Claims, 10 Drawing Sheets

(56) References Cited

U.S. PATENT DOCUMENTS

| | | | | |
|---|---|---|---|---|
| 5,702,484 | A * | 12/1997 | Goymann et al. | 623/23.21 |
| 6,096,084 | A * | 8/2000 | Townley | 623/23.12 |
| 7,156,879 | B1 | 1/2007 | Albrektsson | |
| 7,238,208 | B2 * | 7/2007 | Camino et al. | 623/19.12 |
| 7,879,106 | B2 * | 2/2011 | McMinn | 623/22.44 |
| 2002/0133234 | A1 | 9/2002 | Sotereanos | |
| 2003/0187514 | A1 * | 10/2003 | McMinn | 623/22.44 |
| 2004/0024468 | A1 * | 2/2004 | Lualdi et al. | 623/22.45 |
| 2004/0193275 | A1 * | 9/2004 | Long et al. | 623/19.14 |
| 2004/0225367 | A1 | 11/2004 | Glien et al. | |
| 2005/0197712 | A1 * | 9/2005 | Bigsby et al. | 623/23.27 |
| 2008/0200991 | A1 * | 8/2008 | Collins et al. | 623/23.12 |

FOREIGN PATENT DOCUMENTS

| | | |
|---|---|---|
| EP | 1 240 879 A1 | 9/2002 |
| GB | 2 388 321 A | 11/2003 |
| JP | 4272753 A | 9/1992 |
| JP | 2002-330983 | 11/2002 |
| JP | 2005-511243 | 4/2005 |
| WO | WO 93/01769 A1 | 2/1993 |
| WO | WO 03/051238 A | 6/2003 |
| WO | WO 03/096938 A2 | 11/2003 |
| WO | WO 03/096938 A2 | 11/2003 |

OTHER PUBLICATIONS

First Office Action; Japanese Patent Office; Japanese Patent Application No. 2010-530540, 4 pages.

Chinese Office Action; State Intellectual Property Office of People's Republic of China; Chinese Patent Application No. 200880112837.8, 18 pages.

Second Office Action; Japanese Patent Office; Japanese Patent Application No. 2010-530540; mailed Oct. 1, 2013; 4 pages.

* cited by examiner

JOINT PROSTHESIS

This application is a United States National Phase filing of International Application No. PCT/GB2008/003579 which claims priority to GB Patent Application No. 0720596.6 filed on Oct. 22, 2007, the disclosure of each prior document is incorporated herein by reference in its entirety.

The present invention relates generally to a joint prosthesis, and in particular to a femoral implant, which may be fitted, in use, to a resected femur.

Hip replacements involve the use of an implant stem which is fitted into the medullary canal of the femur. Generally such stems achieve optimum fixation when a tapered prosthesis 10 is fitted in the medullary canal of a tapering bone 11, as shown schematically in FIG. 1. This requirement is generally achieved with a conventional type total hip replacement stem 12 fitted into the proximal femoral portion 13 as shown in FIG. 2.

This form of treatment, however, suffers from the following disadvantages:
1) It requires extensive bone resection of the femoral head and part of the femoral neck.
2) It leads to loading of the shaft of the femur in a non-physiological fashion, leading to distal load transfer and proximal femoral shaft stress shielding.
3) There can be loosening of the total hip replacement stem, as there is a cantilever effect with the point of loading on the prosthetic femoral head at a distance from the point of fixation in the proximal femoral shaft.

With young, active patients it is now regular practice to insert a more conservative type of hip replacement known as a resurfacing. This type of prosthesis overcomes in major part the three disadvantages listed above. However, some patients are not suitable for hip resurfacing, mainly on account of poor bone in the zenith of the femoral head due to cystic destruction, as shown at 14 of FIG. 3. With young patients with such cystic destruction, there is a need for a more conservative type of hip replacement than the standard variety shown in FIG. 2.

The mid head resection procedure is a skilled operation. During a mid head resection procedure, the femur is resected such that the femur has a resected end that is substantially planar. The implant is installed in the resected femur. It is essential that the seating position of the implant is optimised. However, with existing implants it is difficult for the surgeon to determine if the implant is properly seated. If the implant is not properly seated, there is a significant risk of overdrive of the implant, resulting in fracture of the femur and the need for revision surgery, if possible.

The present invention provides an improved femoral implant stem and an improved femoral implant itself.

According to a first aspect of the present invention, there is provided an implant stem for implantation in a femur, comprising: a base portion disposed at the proximal end of the stem and a stem portion extending to the distal end of the stem, wherein the base portion has an engagement means for engaging, in use, with the resected end of the femur.

The engagement means has the advantage that in use it engages with the resected end section of the femur so that the surgeon knows that the implant is correctly seated in the femur. That is, the engagement means indicates a stop point to assist the surgeon during the operation. This is of key importance because if the implant base portion is incorrectly seated during the surgical procedure, the implant is not optimally positioned and the implant may cause the femoral neck to fracture. This is clearly detrimental to the patient and may lead to revision surgery.

The engagement means primarily provides an indication of a stop point for the surgeon, as described above. The indication may be visual, wherein the surgeon can see that the engagement means has properly engaged the resected end of the femur. The indication means may be tactile, wherein the surgeon can feel that the engagement means has properly engaged the resected end of the femur. In each case, the surgeon knows that the implant is optimally seated and that no further impaction is required.

The optimal seating position of the implant stem is at the mid-point of the femoral head. The seating position may vary between 20 mm distally or 20 mm proximally of the mid-point of the femoral head. This maximises bone preservation, which is clearly of fundamental importance.

The engagement means may also prevent distal migration of the implant stem, in use. The engagement means contacts the resected end of the femur and thereby stops further movement of the implant stem in a distal direction.

The engagement means may facilitate bone loading. The engagement means contacts the resected end of the femur and thereby transfers load into the femur.

The engagement means may extend substantially perpendicular to the longitudinal axis of the stem. For example, the engagement means may be disposed around 90 degrees to the longitudinal axis.

The engagement means may have an angular range about the perpendicular. For example, the engagement means may be oriented at 80-100 degrees with respect to the longitudinal axis. The engagement means may be oriented at 85-95 degrees with respect to the longitudinal axis.

The engagement means may be any suitable shape. For example, the engagement means may be one or more flanges. The engagement means may be one or more collars. The engagement means may be one or more plates. The engagement means may be one or more radial discs. The engagement means may be one or more lobes. The engagement means may be one or more tabs. The engagement means may be one or more lips.

The engagement means may extend at least in part around the proximal end of the base portion.

The engagement means may comprise a single engagement means that extends partially around the proximal end of the base portion.

The engagement means may comprise a plurality of engagement means that extend around the proximal end of the base portion.

The engagement means may extend continuously around the proximal end of the base portion.

The engagement means may have a width of 2-10 mm. The engagement means may have a width of 2-8 mm. The engagement means may have a width of 2-6 mm. The engagement means may have a width of 2-4 mm.

The base portion may have an external diameter of 20-50 mm. The base portion may have an external diameter of 20-45 mm. The base portion may have a diameter of 24-42 mm.

The proximal area of the stem may have a textured surface. The proximal area of the stem may have a bone in-growth surface. For example, the proximal area of the stem may comprise beads, such as the Porocast®, surface. The proximal area of the stem may be bead or grit blasted.

The proximal area of the stem may have a coating that promotes bone in-growth. The coating may comprise hydroxy apatite (HA).

Preferably, the proximal area of the stem is titanium bead sintered and HA coated.

The proximal area of the stem may have a smooth finish. The proximal area of the stem may be without beads. The proximal area of the stem may be uncoated.

The stem portion may have a smooth surface.

The stem portion may comprise at least one anti-rotation means. The anti-rotation means may comprise one or more blades, fins, flutes, splines, ribs and/or grooves.

The at least one anti-rotation means may be oriented substantially parallel to the longitudinal axis of the stem.

The anti-rotation means may be oriented in a direction substantially perpendicular to the longitudinal axis of the stem.

The anti-rotation means may be disposed in a substantially helical configuration.

The anti-rotation means may also minimise/prevent migration of the implant.

The stem portion may have a textured surface. The stem portion may have a bone in-growth surface. For example, the stem portion may comprise beads, such as the Porocast® surface. The stem portion may be bead or grit blasted.

The proximal end of the stem may have a coating that promotes bone in-growth. The coating may comprise hydroxyapatite (HA).

The stem portion may have a smooth finish. The stem portion may be without beads. The stem portion may be uncoated.

The stem portion may be cemented in place or modified for suitable biological fixation, in use.

The stem portion may be straight.

The stem portion may be curved.

According to some embodiments of the present invention, there is provided an implant according to the first aspect further comprising a section from which the stem portion extends, said section having an external surface which is of conical or substantially conical form, wherein said section tapers towards said stem portion, said section terminates at the base portion.

According to some embodiments of the present invention, said section, at its maximum diameter, may be substantially the same diameter as the inner diameter of the resected head into which said stem is to be inserted, in use.

According to preferred embodiments of the present invention, the external surface of said section is discontinuous with the surface of the engagement means. That is, there is preferably a discontinuity between the external surface of said section and the surface of the engagement means. For example, the external surface of said section and the surface of the engagement means may not be co-linear (see for example FIG. 4).

According to a preferred embodiment of the present invention, there is provided an implant according to the first aspect further comprising a section from which the stem portion extends, said section having an external surface which is of conical or substantially conical form, wherein said section tapers towards said stem portion, said section terminates at the base portion, and at its maximum diameter, extends substantially away from, and is substantially the same diameter as, the inner diameter of the resected head into which said stem is to be inserted, in use.

In this present disclosure, the term conical may mean conical or substantially conical. It may also mean frustoconical or substantially frustoconical. It may also mean partial toroid or substantially partial toroid.

According to some embodiments of the present invention, there is provided a substantially cylindrical section disposed between the conical section and the stem portion. The substantially cylindrical section may be disposed between the conical section and the anti-rotation means disposed on the stem portion.

The cylindrical section assists in centralisation of the stem during implantation. That is, the cylindrical section minimises the risk of the stem "drifting" away from the centre line during impaction of the implant stem. The cylindrical section is designed to eliminate drift and enable the stem to follow the cut profile.

According to some embodiments of the present invention, there is provided a tapered section disposed between the conical section and the stem portion. The tapered section may be disposed between the conical section and the anti-rotation means disposed on the stem portion.

The cylindrical or tapered portion may be 1-20 mm in length. The cylindrical or tapered portion may be 5-15 mm in length. The cylindrical or tapered portion may be 8-12 mm in length.

The implant of the first aspect may further comprise a connector for connecting a modular femoral head to the implant stem, in use.

The connector may be a taper/spigot. The taper may extend from the proximal end of the stem. The taper may have a conical external surface.

The taper may have a threaded bore down its centre for enabling impaction or extraction of the implant stem with the same tool.

The taper may be a standard taper for use with modular femoral heads in size ranges such as 20-80 mm in diameter.

The implant stem may be made of any suitable material. The implant stem may be made of metal. The implant stem may be made of stainless steel. The implant stem may be made of titanium.

The implant stem may be made of metal alloy. The implant stem may be made of a titanium alloy. The implant stem may be made of cobalt chrome.

The modular heads may be made from any suitable material. The heads may be made of metal. For example, the heads may be made of titanium or stainless steel.

The heads may be made of metal alloy. For example, the heads may be made of cobalt chrome.

The modular heads may be made from ceramic. For example, the modular heads may comprise zirconium containing ceramic materials.

The modular head may be made from a polymer. For example, the modular heads may be made form polyethylene or polypropylene.

According to a second aspect of the present invention, there is provided an implant for implantation in a femur, comprising: a stem according to the first aspect of the present invention and a femoral head.

The stem component may have any of the features described above in relation to the first aspect of the present invention, as appropriate.

The femoral head may be releasably attached to the stem.

The femoral head may be fixedly attached to the stem. The implant may be produced as a single component i.e. a monobloc.

The femoral head may have a size in the range 20-80 mm in diameter.

The implant may be made of any suitable material. The implant may be made of metal. The implant may be made of stainless steel. The implant may be made of titanium.

The implant may be made of metal alloy. The implant may be made of cobalt chrome.

The femoral head may be made from ceramic. For example, the femoral head may comprise zirconium containing ceramic materials.

According to a third aspect of the present invention, there is provided an implant for implantation in a femur, comprising:
an implant stem comprising: a base portion disposed at the proximal end of the stem and a stem portion extending to the distal end of the stem, wherein the base portion has an engagement means for engaging, in use, with the resected end of the femur; and a section from which the stem portion extends, said section having an external surface which is of conical or substantially conical form, wherein said section tapers towards said stem portion, said section terminates at the base portion, and at its maximum diameter is substantially the same diameter as the inner diameter of the resected head into which said stem is to be inserted, in use; and
a femoral head.

The implant stem component may have any of the features described above in relation to the first aspect of the present invention, as appropriate.

The femoral head component may have any of the features described above in relation to the second aspect of the present invention, as appropriate.

According to a fourth aspect of the present invention, there is provided an implant for implantation in a femur according to the second aspect of the present invention, further comprising a section from which the stem portion extends, said section having an external surface which is of conical or substantially conical form, wherein said section tapers towards said stem portion, said section terminates at the base portion, and at its maximum diameter, extends substantially away from, and is substantially the same diameter as, the end surface of the resected head into which said stem is to be inserted, in use.

The implant may have any of the features described above in relation to the first or second aspects of the present invention, as appropriate.

According to a fifth aspect of the present invention, there is provided an implant for implantation in a femur, comprising:
an implant stem comprising: a base portion disposed at the proximal end of the stem and a stem portion extending to the distal end of the stem, wherein the base portion has an engagement means for engaging, in use, with the resected end of the femur; and a section from which the stem portion extends, said section having an external surface which is of conical or substantially conical form, wherein said section tapers towards said stem portion, said section terminates at the base portion, and wherein the external surface of said section is discontinuous with the surface of the engagement means; and
a femoral head.

According to a sixth aspect of the present invention, there is provided a method for implanting an implant in a femur, comprising the steps of:
providing an implant according to any of the first, second, third, fourth or fifth aspects of the present invention;
resecting the femur; and
implanting the implant in the resected femur.

Preferably, the femoral head is resected. The femoral head may be resected at or near to its mid-point.

Reference will now be made, by way of example, to the accompanying drawings in which.

Figure 3:
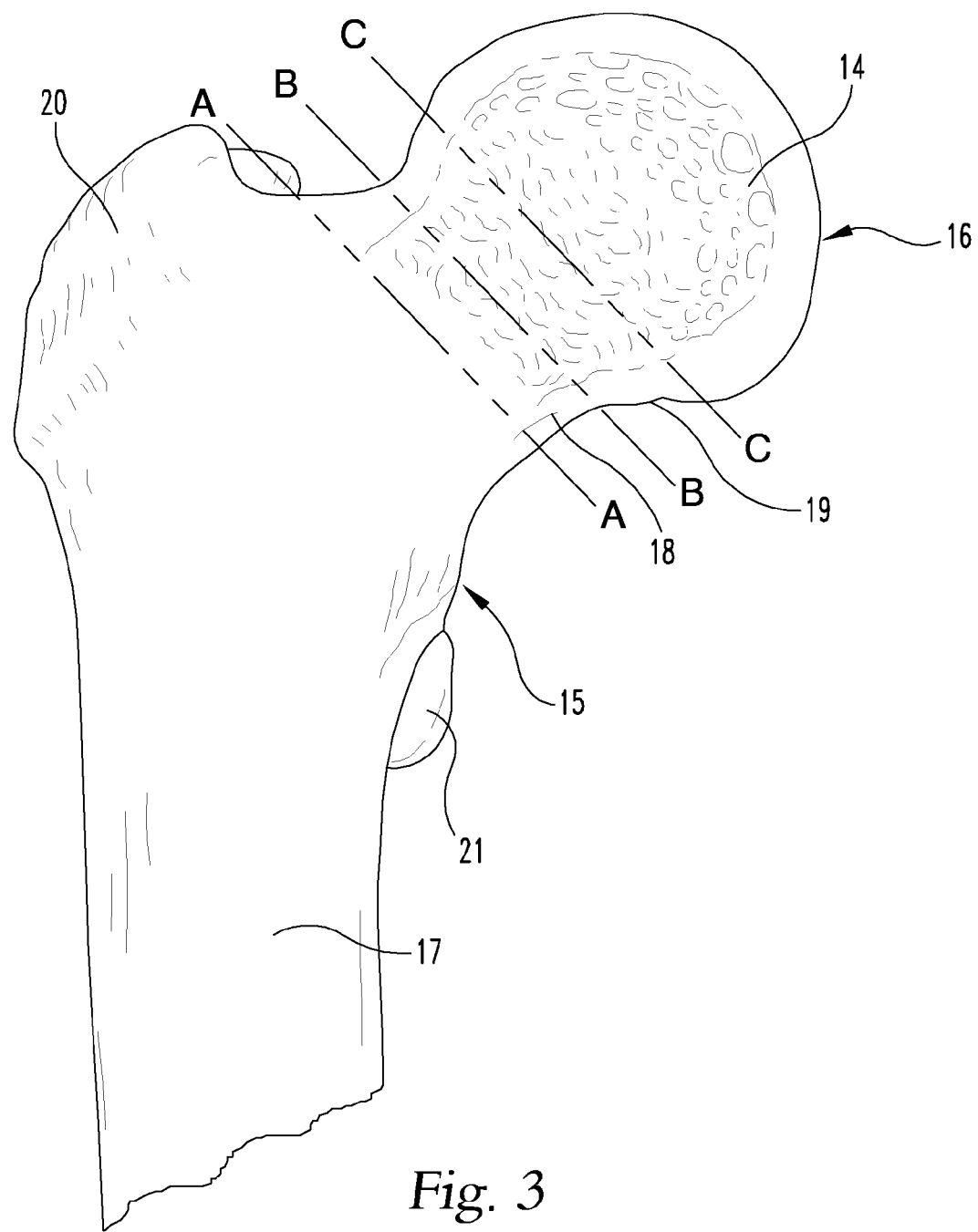
FIG. 3 shows the proximal end of a femur, with three different positions of the level of resecting shown at A-A, B-B and C-C, respectively.

FIG. 3 shows the proximal end of a femur 15. The femur has a head 16 which is globular and forms rather more than a hemisphere. Connecting the head with the main shaft 17 of the femur is a neck 18, the transition between the head 16 and neck 18 being generally smoothly concavely curved as shown at 19. The superior border of the neck terminates at the great trochanter 20, whilst the inferior border of the neck terminates at the lesser trochanter 21.

In FIG. 3, the line A-A represents the resection level for a conventional total hip replacement, this section being taken towards the end of the neck furthest from the head 11. Line B-B represents the resection level for another known hip replacement, this lying through the neck at or adjacent transition area 19 between the head and neck of the femur.

Figure 1:
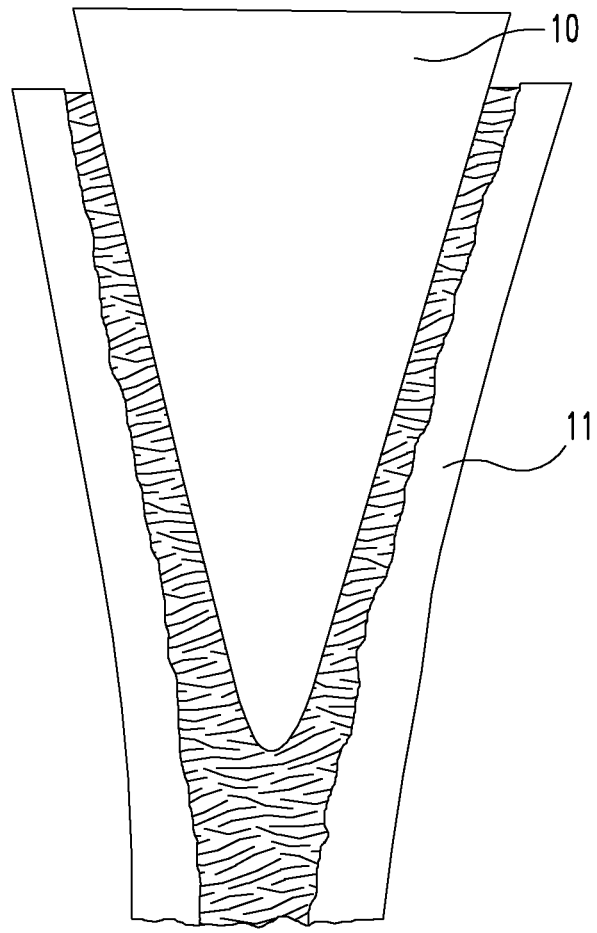
FIG. 1 is a schematic view of an optimum fixation arrangement of a femoral prosthesis.
Figure 2:
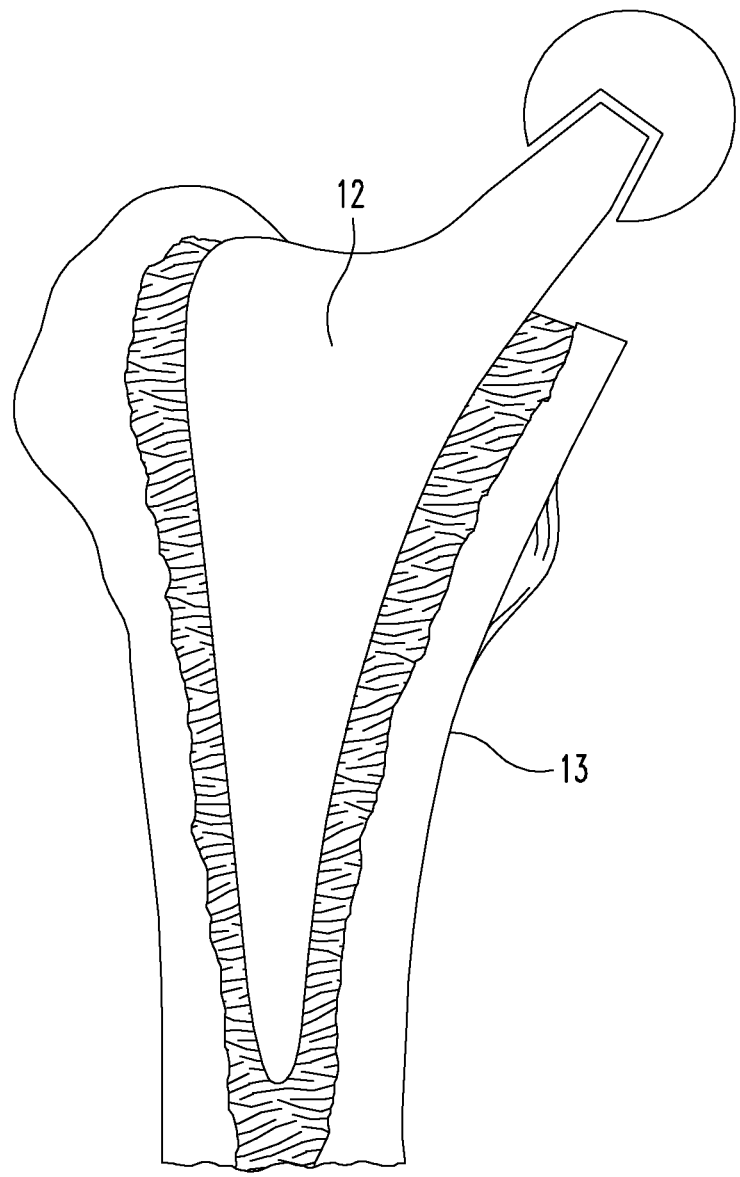
FIG. 2 is a similar view to FIG. 1, showing the fixing of a conventional type of total hip replacement stem.

With an implant of the present invention, the resectioning is not carried out at a level through the neck 18, but instead is carried out through the femoral head. Accordingly, the line C-C represents the resection level for some embodiments of the present invention. By resecting along the line C-C through the base of the femoral head, bone in the transition area between the femoral head and the femoral neck is retained, thus providing the opportunity for exploiting the requirements referred to in relation to FIG. 1.

Accordingly, the first stage in the hip replacement method is to resect the proximal end of the femur at a level through the head 16, for example at the line C-C. By resecting the bone at this position through the base of the femoral head, it is possible then to machine the interior of the bone into the form of a truncated cone, i.e. in the form of an engine valve seating, with this conical or generally conical form of cavity produced thus fulfilling the requirements set out in relation to FIG. 1.

Figure 4:
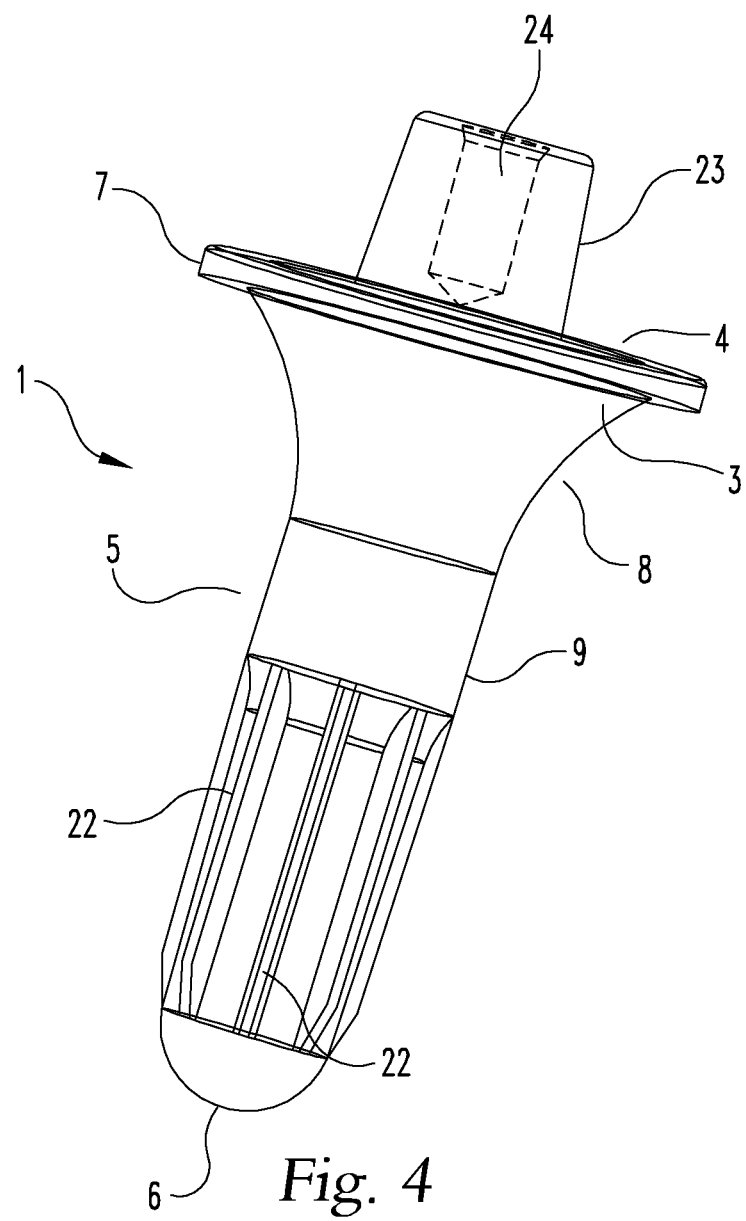
FIG. 4 shows an implant stem in accordance with an embodiment of the present invention.
Figure 5:
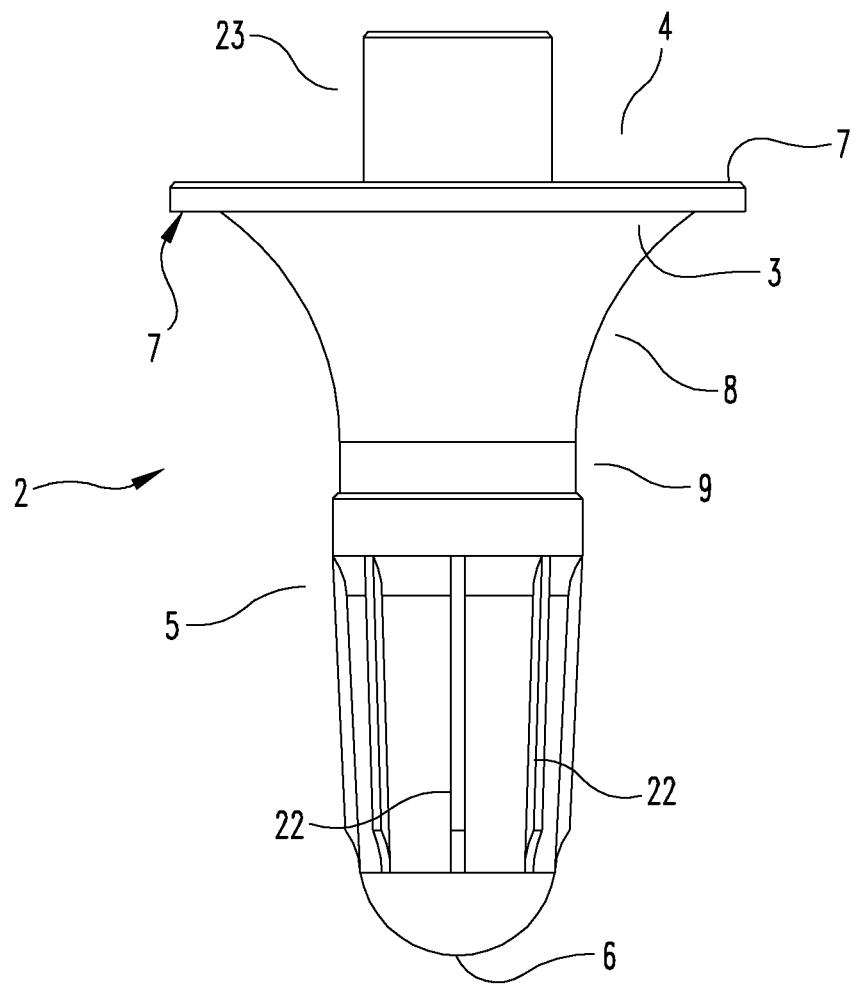
FIG. 5 shows an implant stem in accordance with an embodiment of the present invention.

FIGS. 4 and 5 show implant stems (1 and 2, respectively) in accordance with some embodiments of the present invention. The implant stems 1, 2 comprise a base portion 3 disposed at the proximal end 4 of the stem 1, 2. A stem portion 5 extends to the distal end 6 of the stem. The base portion 3 has an engagement means 7 for engaging, in use, with the resected end of the femur. In the embodiments shown, the engagements means 7 is in the form of a collar extending around the periphery of the base portion 3.

The implant stems 1, 2 comprise a conical shaped section 8, which tapers towards the stem portion 5 and terminates at the base portion 3. The conical section 8, at its maximum diameter, extends substantially away from, and is substantially the same diameter as, the inner diameter of the resected head into which the stem is to be inserted, in use.

The implant stems 1, 2 comprise a substantially cylindrical section 9 disposed between the conical section 8 and the stem portion 5. The cylindrical section 9 assists in the centralisation of the stem 1, 2 during implantation.

The implant stems 1, 2 comprise anti-rotation means 22. In the embodiments shown in FIGS. 4 and 5, the anti-rotation means 22 are in the form of blades/fins oriented substantially parallel to the longitudinal axis of the stem.

The implant stems 1, 2 comprise a connector 23 for connecting a modular femoral head 25 (see FIGS. 7 and 8) to the implant stem. In the embodiments shown in FIGS. 4 and 5, the connector is in the form of a taper. The implant stem 1 of FIG. 4 comprises a taper 23 having a threaded bore 24 down its centre. This enables a surgeon to impact or extract the implant stem using the same tool.

Figure 6:
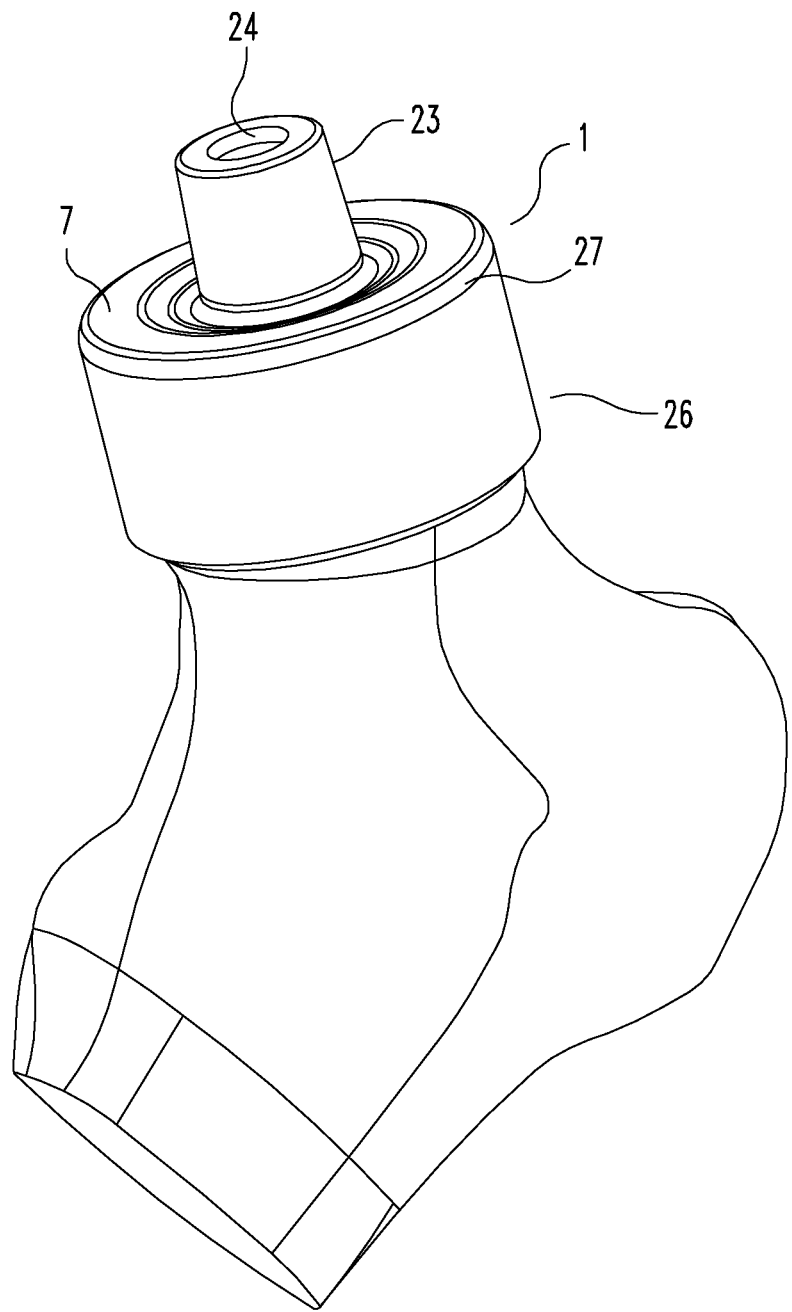
FIG. 6 shows an implant stem in accordance with an embodiment of the present invention implanted in a resected femur.
Figure 7:
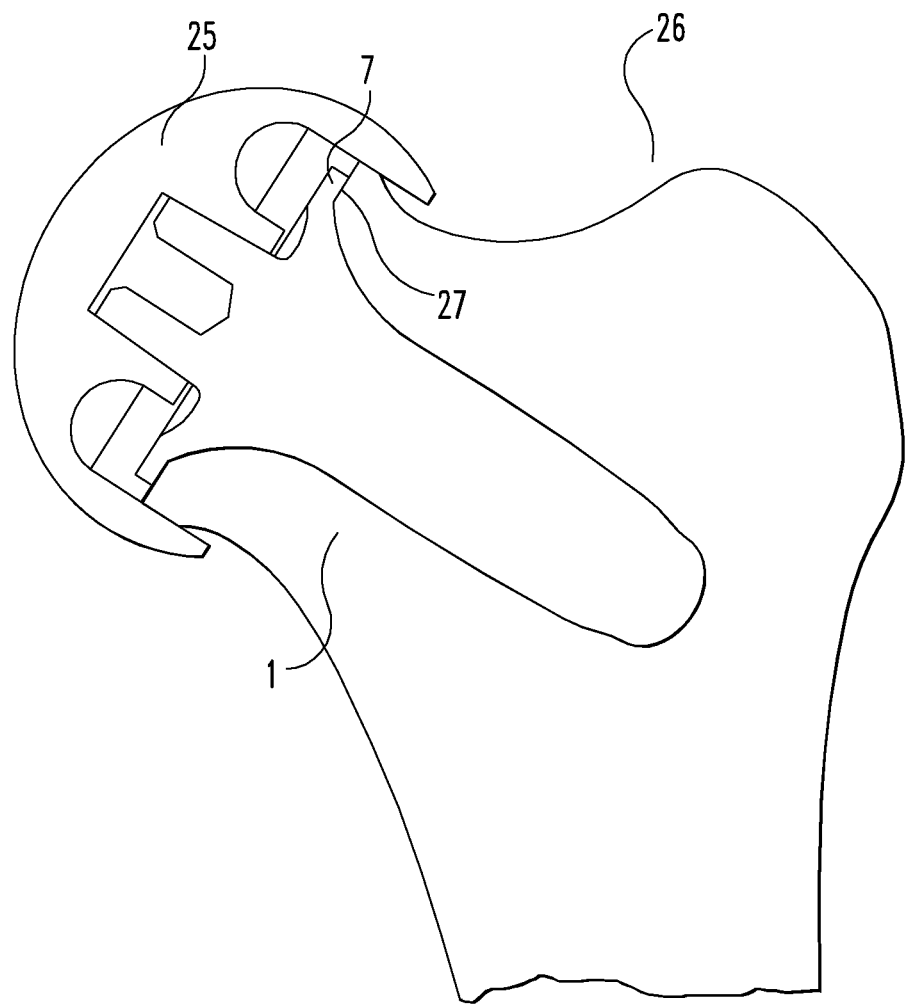
FIG. 7 shows an implant stem and modular femoral head in accordance with an embodiment of the present invention implanted in a resected femur.
Figure 8:
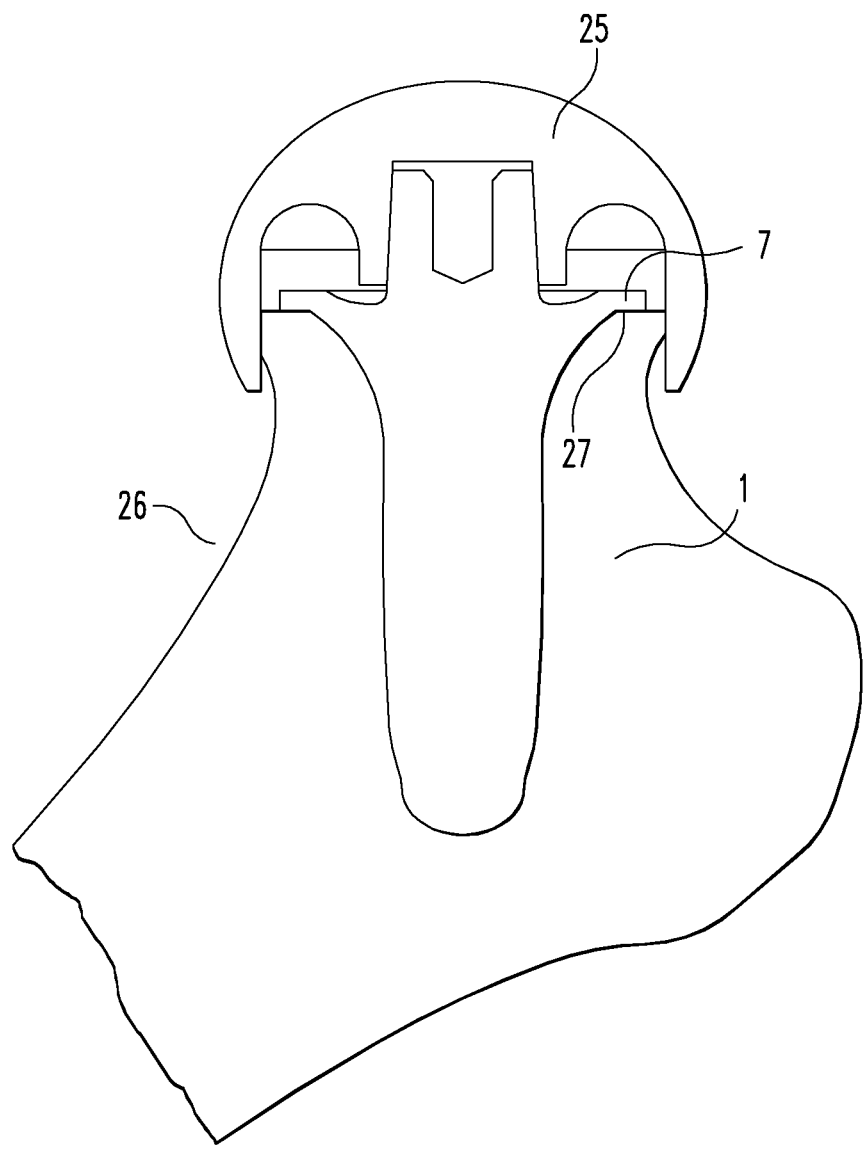
FIG. 8 shows an implant stem and modular femoral head in accordance with an embodiment of the present invention implanted in a resected femur.

FIGS. 6-8 show implant stem 1 implanted into a resected femur 26. The femur 26 has been resected in accordance with the mid head resection procedure. The engagement means 7 engages with the resected end 27 of the femur 26. The engagement means thereby indicates a stop point to the surgeon. Implant stem 1 is shown in FIG. 6 without a femoral head. Implant stem 1 is shown in FIGS. 7 and 8 with a modular femoral head 25 attached. FIG. 8 shows the implant stem oriented in more neutral position than that in FIG. 7.

Figure 9:
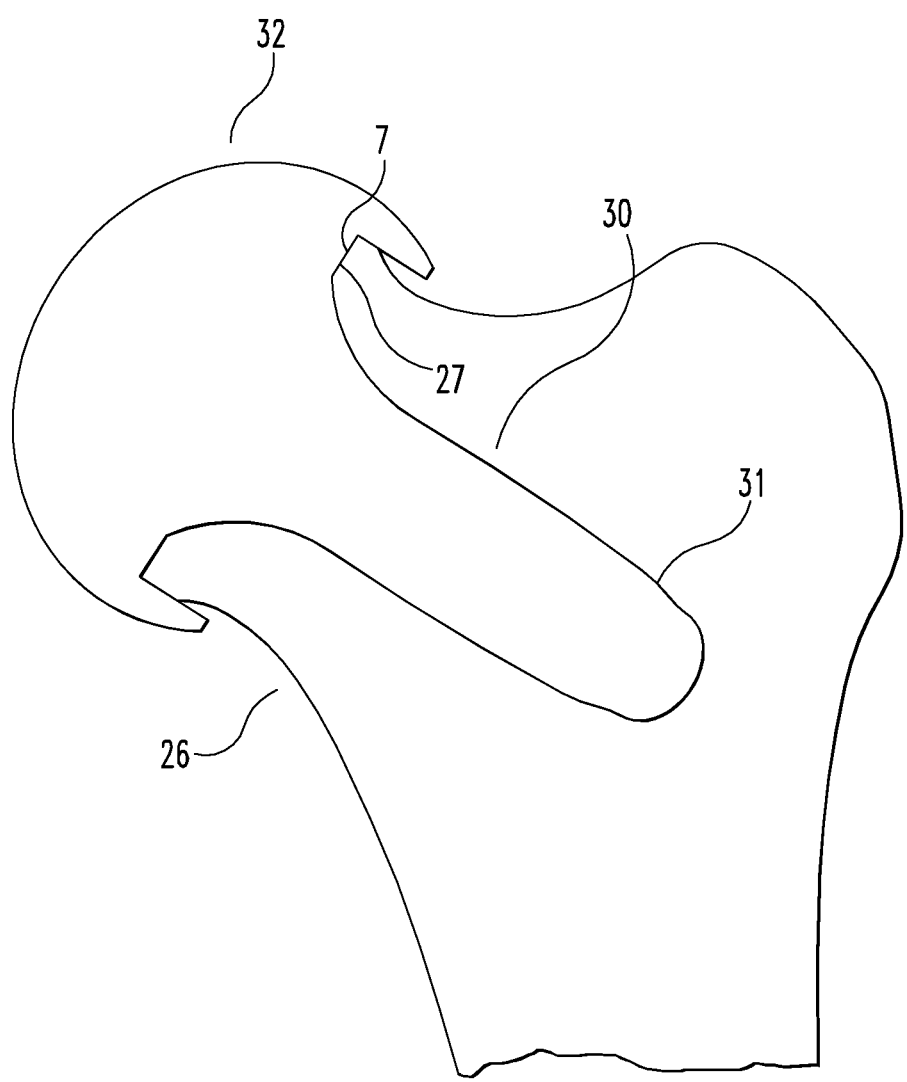
FIG. 9 shows a one-piece femoral implant in accordance with an embodiment of the present invention implanted in a resected femur.
Figure 10:
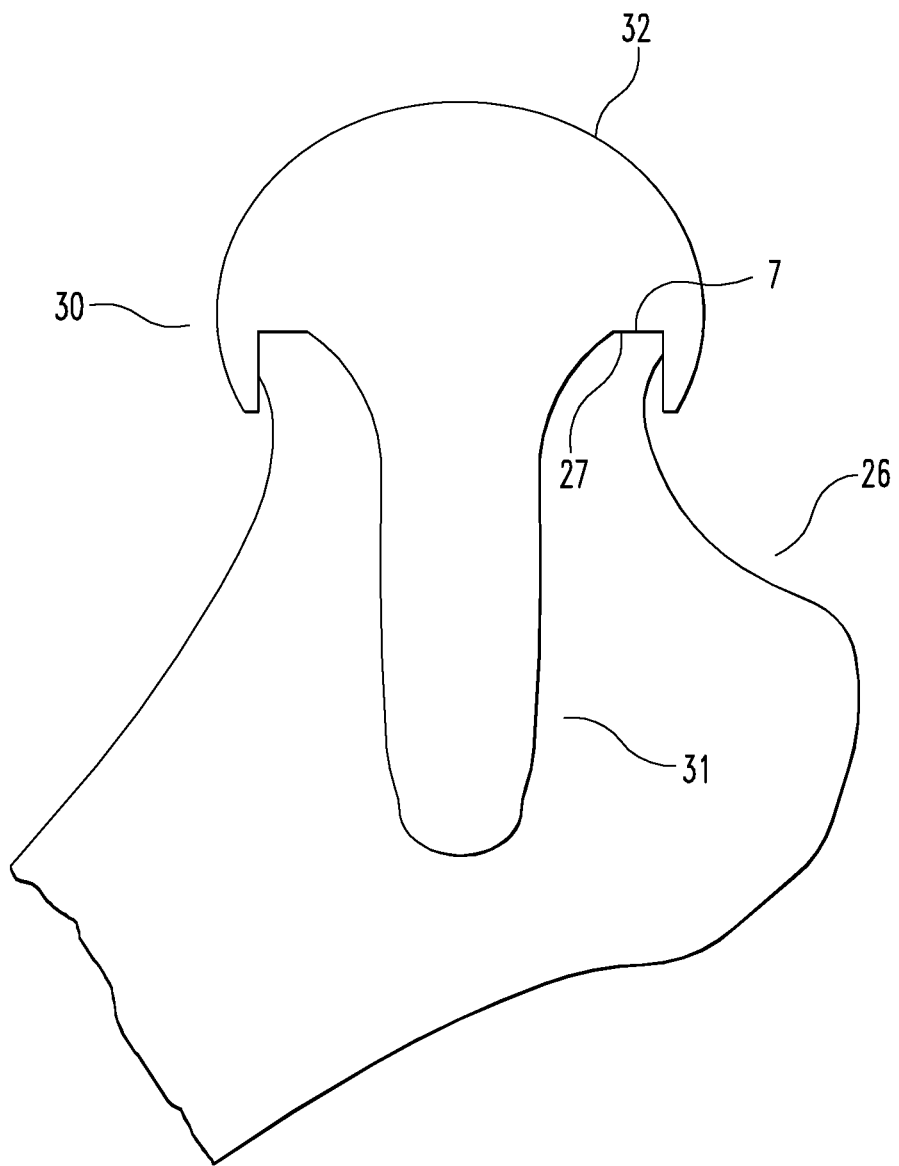
FIG. 10 shows a one-piece femoral implant in accordance with an embodiment of the present invention implanted in a resected femur.

FIGS. 9 and 10 show a one-piece femoral implant 30. The femoral implant comprises an implant stem 31 like that in FIGS. 4 to 8 in combination with a femoral head 32. The engagement means 7 engages with the resected end 27 of the femur 26. The engagement means thereby indicates a stop point to the surgeon. FIG. 10 shows the implant 30 oriented in a more neutral position than that in FIG. 9.

What is claimed is:

1. An implant for implantation in a femur, comprising:
    an implant stem comprising:
        a base portion disposed at a proximal end of the stem and a stem portion extending to a distal end of the stem, wherein the base portion has an engagement means for engaging a resected head of the femur and defining a distally-facing bone engagement surface structured for engagement with the resected head of the femur to thereby provide the implant with a single stop point to limit insertion of the stem portion into the resected head of the femur; and
        a tapered portion having an external tapered surface of conical or substantially conical form, said tapered surface extending from said stem portion and terminating at said distally-facing bone engagement surface such that said bone engagement surface defines a lip extending beyond said tapered surface, and wherein said tapered surface of said tapered portion is discontinuous with said distally-facing bone engagement surface of said engagement means so as to define a surface discontinuity; and
    a modular femoral head; and
    wherein said bone engagement surface defining said single stop point and said lip is defined by said implant stem and not by said modular femoral head;
    wherein said modular femoral head is releasably attached to said implant stem by a connector extending from said base portion of said implant stem;
    wherein said base portion of said implant stem does not include any portion extending distally beyond said distally-facing bone engagement surface defined by said lip, and said modular femoral head extending distally beyond said lip when attached to said implant stem; and
    wherein said modular femoral head is detached from said implant stem during said engagement of said bone engagement surface with the resected head of the femur to thereby provide an indication of proper engagement of said bone engagement surface defined by said lip with the resected head of the femur.

2. An implant according to claim 1, wherein a proximal area of the stem comprises a bone in-growth surface.

3. An implant according to claim 1, wherein the stem portion comprises a bone in-growth surface.

4. An implant according to claim 1, wherein the stem portion comprises at least one anti-rotation means.

5. An implant according to claim 1, wherein said tapered surface has a maximum diameter that is configured to be substantially the same as an inner diameter of the resected head into which said stem is to be inserted.

6. An implant according to claim 1, wherein said connector comprises a projection extending from said base portion of said implant stem, said projection positioned within an opening in said modular femoral head to releasably attach said modular femoral head to said implant stem.

7. An implant according to claim 6, wherein said projection is tapered and defines a conical external surface.

8. An implant according to claim 6, wherein said projection defines an internally threaded bore configured for threaded engagement with an insertion/removal tool.

9. An implant according to claim 1, wherein said modular femoral head is spaced from and does not contact said lip of said implant stem.

10. An implant according to claim 1, wherein said indication of proper engagement of said bone engagement surface of said lip with the resected head of the femur comprises a direct visual indication.

11. An implant according to claim 1, wherein said external tapered surface of said tapered portion of said implant stem comprises a concave curvature extending from said stem portion to said distally-facing bone engagement surface of said lip.

12. An implant for implantation in a femur, comprising:
    an implant stem comprising:
        a base portion disposed at a proximal end of the stem and a stem portion extending to a distal end of the stem, wherein the base portion has an engagement means for engaging a resected head of the femur and defining a distally-facing bone engagement surface structured for engagement with the resected head of the femur to thereby provide the implant with a single stop point to limit insertion of the stem portion into the resected head of the femur; and
        a tapered portion from which the stem portion extends, said tapered portion having an external tapered surface which is of conical or substantially conical form, wherein said tapered surface tapers from said base portion towards said stem portion and terminates at said bone engagement surface such that said bone engagement surface defines a lip extending beyond said tapered surface, and wherein the external tapered surface of said tapered portion is discontinuous with the distally-facing bone engagement surface of the engagement means so as to define a surface discontinuity; and
    a modular femoral head; and
    wherein said bone engagement surface defining said single stop point and said lip is defined by said implant stem and not by said modular femoral head;

wherein said modular femoral head is releasably attached to said implant stem by a connector extending from said base portion of said implant stem;

wherein said base portion of said implant stem does not include any portion extending distally beyond said distally-facing bone engagement surface defined by said lip, and said modular femoral head extending distally beyond said lip when attached to said implant stem; and wherein said modular femoral head is detached from said implant stem during said engagement of said bone engagement surface with the resected head of the femur to thereby provide a direct visual indication of proper engagement of said bone engagement surface defined by said lip with the resected head of the femur.

13. An implant according to claim 12, wherein said connector comprises a projection extending from said base portion of said implant stem, said projection positioned within an opening in said modular femoral head to releasably attach said modular femoral head to said implant stem.

14. An implant according to claim 13, wherein said projection is tapered and defines a conical external surface.

15. An implant according to claim 13, wherein said projection defines an internally threaded bore configured for threaded engagement with an insertion/removal tool.

16. An implant according to claim 12, wherein said modular femoral head is spaced from and does not contact said lip of said implant stem.

17. An implant according to claim 12, wherein said indication of proper engagement of said bone engagement surface of said lip with the resected head of the femur further comprises a tactile indication.

18. An implant according to claim 12, wherein said external tapered surface of said tapered portion of said implant stem comprises a concave curvature extending from said stem portion to said distally-facing bone engagement surface of said lip.

* * * * *